(12) United States Patent
Haagsman et al.

(10) Patent No.: US 11,603,391 B2
(45) Date of Patent: *Mar. 14, 2023

(54) CATH2 DERIVATIVES

(71) Applicant: Universiteit Utrecht Holding B.V., Utrecht (NL)

(72) Inventors: Hendrik Peter Haagsman, Utrecht (NL); Albert van Dijk, Utrecht (NL); Edwin Johannes Adrianus Veldhuizen, Utrecht (NL)

(73) Assignee: Universiteit Utrecht Holding B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/069,127

(22) Filed: Oct. 13, 2020

(65) Prior Publication Data

US 2021/0246177 A1 Aug. 12, 2021

Related U.S. Application Data

(63) Continuation of application No. 15/310,034, filed as application No. PCT/NL2015/050323 on May 8, 2015, now Pat. No. 10,829,524.

(30) Foreign Application Priority Data

May 9, 2014 (EP) .................................... 14167718

(51) Int. Cl.
C07K 2/00 (2006.01)
C07K 14/465 (2006.01)
A61K 38/00 (2006.01)

(52) U.S. Cl.
CPC ............ *C07K 14/465* (2013.01); *A61K 38/00* (2013.01)

(58) Field of Classification Search
CPC ....... A61K 49/00; A61K 39/00; C07K 14/465
USPC ............................................ 424/184.1, 185.1
See application file for complete search history.

(56) References Cited

U.S. PATENT DOCUMENTS 10,829,524 B2 * 11/2020 Haagsman ................ A61P 3/02
2008/0119405 A1 5/2008 Zhang et al.

FOREIGN PATENT DOCUMENTS

| JP | 2004506019 | 2/2004 |
| JP | 2007513138 | 5/2007 |
| JP | 2010516688 | 5/2010 |
| RU | 2126267 C1 | 6/1996 |
| RU | 2007103151 A | 1/2007 |
| RU | 2458526 C1 | 8/2012 |
| WO | WO 2009/010968 A2 | 1/2009 |
| WO | WO 2010/093245 A1 | 8/2010 |

OTHER PUBLICATIONS

Molhoek et al., "Improved proteolytic stability of chicken cathelicidin-2 derived peptides by D-amino acid substitutions and cyclization," Peptides, 32:875-880 (2011).
Van Dijk et al., "Identification of chicken cathelicidin-2 core elements involved in antibacterial and immunomodulatory activities," Molecular Immunology, 46:2465-2473 (2009).
Xiao et al., "The Central Kink Region of Fowlicidin-2, an α-Helical Host Defense Peptide, Is Critically Involved in Bacterial Killing and Endotoxin Neutralization," Journal of Innate Immunity, 1:268-280 (2009).
International Search Report for PCT/NL2015/050323, dated Sep. 28, 2015.
Written Opinion of the International Searching Authority for PCT/NL2015/050323, dated Sep. 28, 2015.
Dijk A. V. et al., "Avian cathelicidins: Paradigms for the development of anti-infectives," Veterinaiy Microbiology, 2011, vol. 153, pp. 27-36.
Van DijK, A., et al., "Veterinary Immunology and Immunopathology," vol. 106, No. 3-4, pp. 321-327, 2005.
Negash, T. et al., "Veterinary Quarterly," vol. 26, No. 2:76-87 (2004).

* cited by examiner

*Primary Examiner* — Albert M Navarro
*Assistant Examiner* — Mark Navarro
(74) *Attorney, Agent, or Firm* — Fish & Richardson P.C.

(57) ABSTRACT

The present invention provides new derivatives of CATH2 or CMAP27, one of the cathelicidins. These derivatives comprise N-terminally truncated peptides, cyclic peptides, D-amino acid variants of CATH2 and its truncated derivatives, inverso and retroinverso CATH2 derivatives. These derivatives are useful as anti-infectives, in vaccines, and especially for in ovo applications. Further, for the above derivatives and also for the already known C-terminally truncated derivatives new immunoactivating functions have been described that are particularly advantageous for prophylactic treatments.

10 Claims, 8 Drawing Sheets

Figures 1A, 1B:
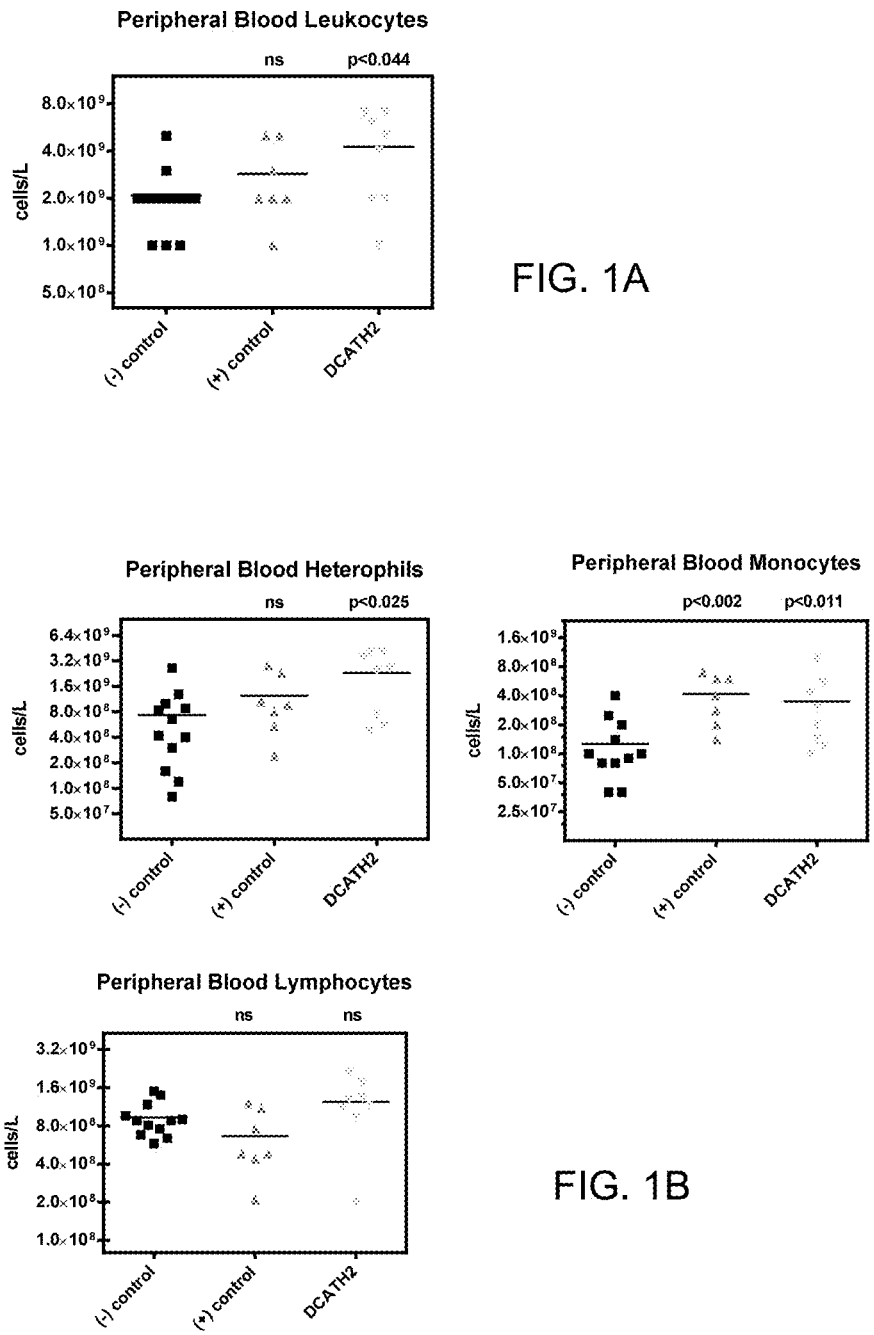

Specification includes a Sequence Listing.

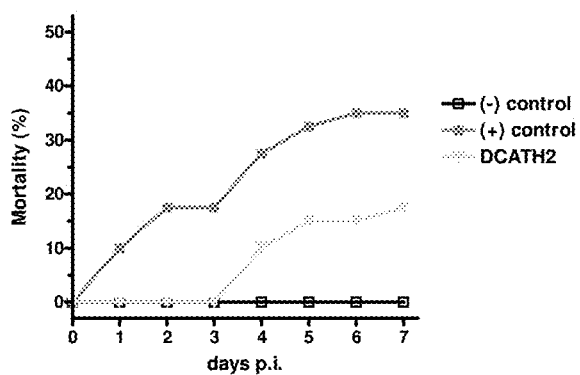
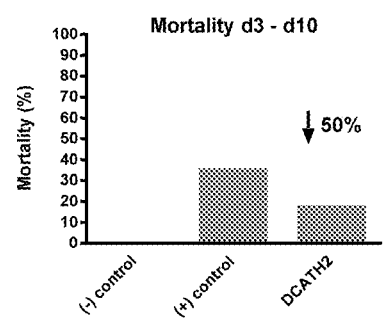
FIG. 2A
FIG. 2B
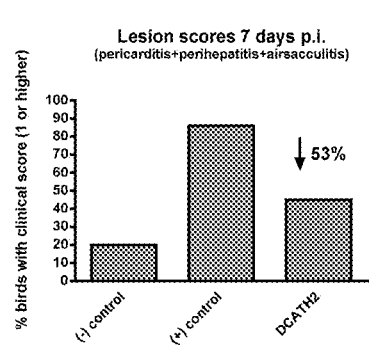
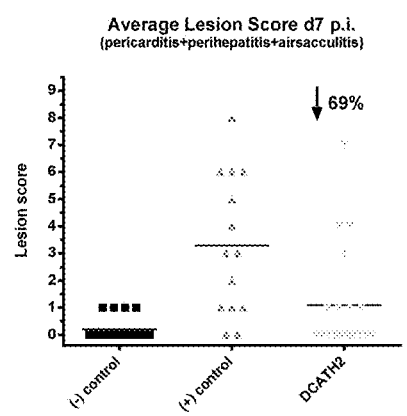
FIG. 3A
FIG. 3B

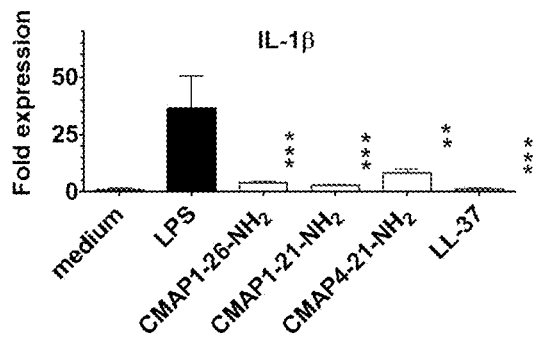
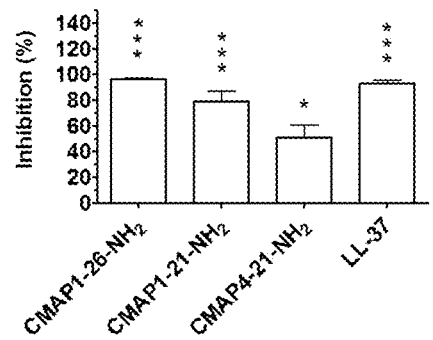
FIG. 11A
FIG. 11B
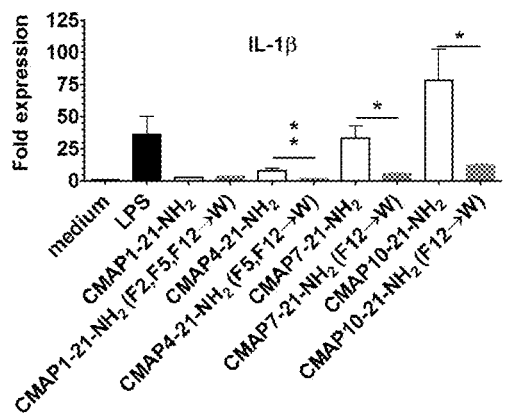
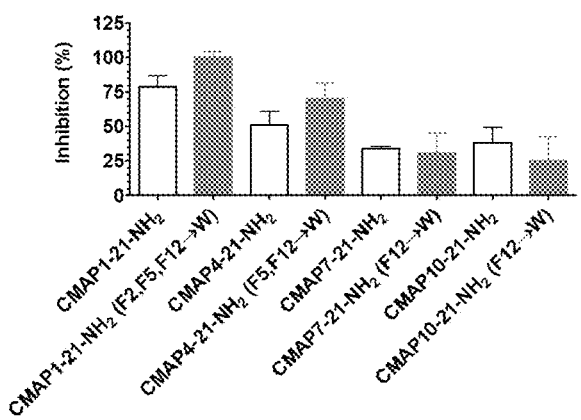
FIG. 12A
FIG. 12B
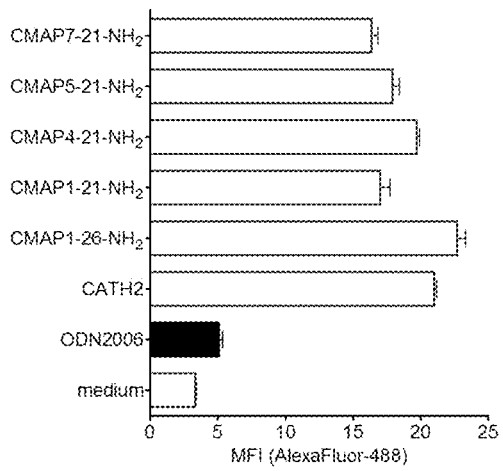
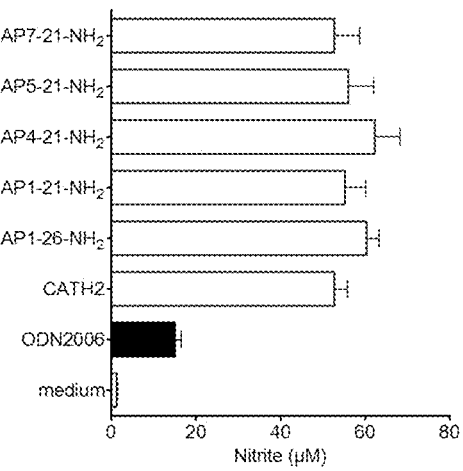
FIG. 13A
FIG. 13B

SEQUENCE LISTING

<160> NUMBER OF SEQ ID NOS: 45

<210> SEQ ID NO 1
<211> LENGTH: 27
<212> TYPE: PRT
<213> ORGANISM: Artificial Sequence
<220> FEATURE:
<223> OTHER INFORMATION: CMAP27

<400> SEQUENCE: 1

Arg Phe Gly Arg Phe Leu Arg Lys Ile Arg Arg Phe Arg Pro Lys Val
1               5                   10                  15

Thr Ile Thr Ile Gln Gly Ser Ala Arg Phe Gly
            20                  25

<210> SEQ ID NO 2
<211> LENGTH: 26
<212> TYPE: PRT
<213> ORGANISM: Artificial Sequence
<220> FEATURE:
<223> OTHER INFORMATION: CMAP1-26
<220> FEATURE:
<221> NAME/KEY: MOD_RES
<222> LOCATION: (26)..(26)
<223> OTHER INFORMATION: amidated

<400> SEQUENCE: 2

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
            20                  25

<210> SEQ ID NO 3
<211> LENGTH: 26
<212> TYPE: PRT
<213> ORGANISM: Artificial Sequence
<220> FEATURE:
<223> OTHER INFORMATION: D-C(1-26)(DCATH2)
<220> FEATURE:
<221> NAME/KEY: MOD_RES
<222> LOCATION: (1)..(26)
<223> OTHER INFORMATION: All amino acids are "D" amino acids
<220> FEATURE:
<221> NAME/KEY: MOD_RES
<222> LOCATION: (26)..(26)
<223> OTHER INFORMATION: amidated

<400> SEQUENCE: 3

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
            20                  25

<210> SEQ ID NO 4
<211> LENGTH: 21
<212> TYPE: PRT
<213> ORGANISM: Artificial Sequence
<220> FEATURE:
<223> OTHER INFORMATION: D-C(1-21)
<220> FEATURE:
<221> NAME/KEY: MOD_RES
<222> LOCATION: (1)..(21)
<223> OTHER INFORMATION: All amino acids are "D" amino acids
<220> FEATURE:
<221> NAME/KEY: MOD_RES
<222> LOCATION: (21)..(21)
<223> OTHER INFORMATION: amidated

<400> SEQUENCE: 4

Arg Phe Gly Arg Phe Leu Arg Lys Ile Arg Arg Phe Arg Pro Lys Val
1               5                   10                  15

Thr Ile Thr Ile Gln
            20

<210> SEQ ID NO 5
<211> LENGTH: 18
<212> TYPE: PRT
<213> ORGANISM: Artificial Sequence
<220> FEATURE:
<223> OTHER INFORMATION: D-C(4-21)
<220> FEATURE:
<221> NAME/KEY: MOD_RES
<222> LOCATION: (1)..(18)
<223> OTHER INFORMATION: All amino acids are "D" amino acids
<220> FEATURE:
<221> NAME/KEY: MOD_RES
<222> LOCATION: (18)..(18)
<223> OTHER INFORMATION: amidated

<400> SEQUENCE: 5

Arg Phe Leu Arg Lys Ile Arg Arg Phe Arg Pro Lys Val Thr Ile Thr
1               5                   10                  15

Ile Gln

<210> SEQ ID NO 6
<211> LENGTH: 15
<212> TYPE: PRT
<213> ORGANISM: Artificial Sequence
<220> FEATURE:
<223> OTHER INFORMATION: D-C(7-21)
<220> FEATURE:
<221> NAME/KEY: MOD_RES
<222> LOCATION: (1)..(15)
<223> OTHER INFORMATION: All amino acids are "D" amino acids
<220> FEATURE:
<221> NAME/KEY: MOD_RES
<222> LOCATION: (15)..(15)
<223> OTHER INFORMATION: amidated

<400> SEQUENCE: 6

Arg Lys Ile Arg Arg Phe Arg Pro Lys Val Thr Ile Thr Ile Gln
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: D-C(7-21)F to W
<220> FEATURE:
<221> NAME/KEY: MOD_RES
<222> LOCATION: (1)..(15)
<223> OTHER INFORMATION: All amino acids are "D" amino acids
<220> FEATURE:
<221> NAME/KEY: MOD_RES
<222> LOCATION: (15)..(15)
<223> OTHER INFORMATION: amidated

<400> SEQUENCE: 7

Arg Lys Ile Arg Arg Trp Arg Pro Lys Val Thr Ile Thr Ile Gln
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: D-C (7-21)F to Y

```
<220> FEATURE:
<221> NAME/KEY: MOD_RES
<222> LOCATION: (1)..(15)
<223> OTHER INFORMATION: All amino acids are "D" amino acids
<220> FEATURE:
<221> NAME/KEY: MOD_RES
<222> LOCATION: (15)..(15)
<223> OTHER INFORMATION: amidated

<400> SEQUENCE: 8

Arg Lys Ile Arg Arg Tyr Arg Pro Lys Val Thr Ile Thr Ile Gln
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: D-C(10-21)F to W
<220> FEATURE:
<221> NAME/KEY: MOD_RES
<222> LOCATION: (1)..(12)
<223> OTHER INFORMATION: All amino acids are "D" amino acids
<220> FEATURE:
<221> NAME/KEY: MOD_RES
<222> LOCATION: (12)..(12)
<223> OTHER INFORMATION: amidated

<400> SEQUENCE: 9

Arg Arg Trp Arg Pro Lys Val Thr Ile Thr Ile Gln
1               5                   10

<210> SEQ ID NO 10
<211> LENGTH: 15
<212> TYPE: PRT
<213> ORGANISM: Artificial Sequence
<220> FEATURE:
<223> OTHER INFORMATION: D-C(1-15)
<220> FEATURE:
<221> NAME/KEY: MOD_RES
<222> LOCATION: (1)..(15)
<223> OTHER INFORMATION: All amino acids are "D" amino acids

<400> SEQUENCE: 10

Arg Phe Gly Arg Phe Leu Arg Lys Ile Arg Arg Phe Arg Pro Lys
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: cycCMAP(1-21)[Lys8]
<220> FEATURE:
<221> NAME/KEY: MOD_RES
<222> LOCATION: (7)..(7)
<223> OTHER INFORMATION: Has an attached
      "Fmoc-L-bishomopropargylglycine"
<220> FEATURE:
<221> NAME/KEY: MOD_RES
<222> LOCATION: (7)..(20)
<223> OTHER INFORMATION: Position 7 and position 20 are connected to
      form a cycle
<220> FEATURE:
<221> NAME/KEY: MOD_RES
<222> LOCATION: (11)..(11)
<223> OTHER INFORMATION: Has an attached "azido-resin"

<400> SEQUENCE: 11

Arg Phe Gly Arg Phe Leu Arg Ile Arg Arg Phe Arg Pro Lys Val Thr
1               5                   10                  15
```

Ile Thr Ile Gln
        20

<210> SEQ ID NO 12
<211> LENGTH: 20
<212> TYPE: PRT
<213> ORGANISM: Artificial Sequence
<220> FEATURE:
<223> OTHER INFORMATION: cycCMAP(1-21)[Arg7]
<220> FEATURE:
<221> NAME/KEY: MOD_RES
<222> LOCATION: (6)..(6)
<223> OTHER INFORMATION: Has an attached
      "Fmoc-L-bishomopropargylglycine"
<220> FEATURE:
<221> NAME/KEY: MOD_RES
<222> LOCATION: (6)..(20)
<223> OTHER INFORMATION: Position 6 and position 20 are connected to
      form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 12

Arg Phe Gly Arg Phe Leu Lys Ile Arg Arg Phe Arg Pro Lys Val Thr
1               5                   10                  15

Ile Thr Ile Gln
        20

<210> SEQ ID NO 13
<211> LENGTH: 20
<212> TYPE: PRT
<213> ORGANISM: Artificial Sequence
<220> FEATURE:
<223> OTHER INFORMATION: cycCMAP(1-21)[Leu6]
<220> FEATURE:
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and position 20 are connected to
      form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 13

Arg Phe Gly Arg Phe Arg Lys Ile Arg Arg Phe Arg Pro Lys Val Thr
1               5                   10                  15

Ile Thr Ile Gln
        20

<210> SEQ ID NO 14
<211> LENGTH: 20
<212> TYPE: PRT
<213> ORGANISM: Artificial Sequence
<220> FEATURE:
<223> OTHER INFORMATION: cycCMAP(1-21)[Leu6],Phe2/Trp
<220> FEATURE:
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and 20 are connected to form a cycle

```
<220> FEATURE:
<221> NAME/KEY: MOD_RES
<222> LOCATION: (20)..(20)
<223> OTHER INFORMATION: Has an attached "azido-resin"

<400> SEQUENCE: 14

Arg Trp Gly Arg Phe Arg Lys Ile Arg Arg Phe Arg Pro Lys Val Thr
1               5                   10                  15

Ile Thr Ile Gln
            20

<210> SEQ ID NO 15
<211> LENGTH: 20
<212> TYPE: PRT
<213> ORGANISM: Artificial Sequence
<220> FEATURE:
<223> OTHER INFORMATION: cycCMAP(1-21)[Leu6],Phe2,5/Trp
<220> FEATURE:
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and 20 are connected to form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 15

Arg Trp Gly Arg Trp Arg Lys Ile Arg Arg Phe Arg Pro Lys Val Thr
1               5                   10                  15

Ile Thr Ile Gln
            20

<210> SEQ ID NO 16
<211> LENGTH: 20
<212> TYPE: PRT
<213> ORGANISM: Artificial Sequence
<220> FEATURE:
<223> OTHER INFORMATION: cycCMAP(1-21)[Leu6],Phe2,5,12/Trp
<220> FEATURE:
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and 20 are connected to form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 16

Arg Trp Gly Arg Trp Arg Lys Ile Arg Arg Trp Arg Pro Lys Val Thr
1               5                   10                  15

Ile Thr Ile Gln
            20

<210> SEQ ID NO 17
<211> LENGTH: 20
<212> TYPE: PRT
<213> ORGANISM: Artificial Sequence
<220> FEATURE:
<223> OTHER INFORMATION: cycCMAP(1-21)[Leu6],Phe5,12/Trp
<220> FEATURE:
```

```
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and 20 are connected to form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 17

Arg Phe Gly Arg Trp Arg Lys Ile Arg Arg Trp Arg Pro Lys Val Thr
1               5                   10                  15

Ile Thr Ile Gln
            20

<210> SEQ ID NO 18
<211> LENGTH: 20
<212> TYPE: PRT
<213> ORGANISM: Artificial Sequence
<220> FEATURE:
<223> OTHER INFORMATION: cycCMAP(1-21)[Leu6],Phe12/Trp
<220> FEATURE:
<221> NAME/KEY: MOD_RES
<222> LOCATION: (5)..(5)
<223> OTHER INFORMATION: Has an attached
      "Fmoc-L-bishomopropargylglycine"
<220> FEATURE:
<221> NAME/KEY: MOD_RES
<222> LOCATION: (5)..(20)
<223> OTHER INFORMATION: Position 5 and 20 are connected to form a cycle
<220> FEATURE:
<221> NAME/KEY: MOD_RES
<222> LOCATION: (20)..(20)
<223> OTHER INFORMATION: Has an attached "azido-resin"

<400> SEQUENCE: 18

Arg Phe Gly Arg Phe Arg Lys Ile Arg Arg Trp Arg Pro Lys Val Thr
1               5                   10                  15

Ile Thr Ile Gln
            20

<210> SEQ ID NO 19
<211> LENGTH: 27
<212> TYPE: PRT
<213> ORGANISM: Artificial Sequence
<220> FEATURE:
<223> OTHER INFORMATION: RI equivalent of CMAP27

<400> SEQUENCE: 19

Gly Phe Arg Ala Ser Gly Gln Ile Thr Ile Thr Val Lys Pro Arg Phe
1               5                   10                  15

Arg Arg Ile Lys Arg Leu Phe Arg Gly Phe Arg
            20                  25

<210> SEQ ID NO 20
<211> LENGTH: 21
<212> TYPE: PRT
<213> ORGANISM: Artificial Sequence
<220> FEATURE:
<223> OTHER INFORMATION: RI-C(1-21)

<400> SEQUENCE: 20

Gln Ile Thr Ile Thr Val Lys Pro Arg Phe Arg Arg Ile Lys Arg Leu
1               5                   10                  15
```

Phe Arg Gly Phe Arg
            20

<210> SEQ ID NO 21
<211> LENGTH: 18
<212> TYPE: PRT
<213> ORGANISM: Artificial Sequence
<220> FEATURE:
<223> OTHER INFORMATION: RI-C(4-21)

<400> SEQUENCE: 21

Gln Ile Thr Ile Thr Val Lys Pro Arg Phe Arg Arg Ile Lys Arg Leu
1               5                   10                  15

Phe Arg

<210> SEQ ID NO 22
<211> LENGTH: 15
<212> TYPE: PRT
<213> ORGANISM: Artificial Sequence
<220> FEATURE:
<223> OTHER INFORMATION: RI-C(7-21)

<400> SEQUENCE: 22

Gln Ile Thr Ile Thr Val Lys Pro Arg Phe Arg Arg Ile Lys Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: RI-C(7-21)F/W

<400> SEQUENCE: 23

Gln Ile Thr Ile Thr Val Lys Pro Arg Trp Arg Arg Ile Lys Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: RI-C(7-21)F/Y

<400> SEQUENCE: 24

Gln Ile Thr Ile Thr Val Lys Pro Arg Tyr Arg Arg Ile Lys Arg
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: RI-C(10-21)F/W

<400> SEQUENCE: 25

Gln Ile Thr Ile Thr Val Lys Pro Arg Trp Arg Arg
1               5                   10

<210> SEQ ID NO 26
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 26

```
Arg Phe Leu Arg Lys Ile Arg Arg Phe Arg Pro Lys Val Thr Ile Thr
1               5                   10                  15

Ile Gln

<210> SEQ ID NO 27
<211> LENGTH: 17
<212> TYPE: PRT
<213> ORGANISM: Artificial Sequence
<220> FEATURE:
<223> OTHER INFORMATION: CMAP27-derivative

<400> SEQUENCE: 27

Phe Leu Arg Lys Ile Arg Arg Phe Arg Pro Lys Val Thr Ile Thr Ile
1               5                   10                  15

Gln

<210> SEQ ID NO 28
<211> LENGTH: 16
<212> TYPE: PRT
<213> ORGANISM: Artificial Sequence
<220> FEATURE:
<223> OTHER INFORMATION: CMAP27-derivative

<400> SEQUENCE: 28

Leu Arg Lys Ile Arg Arg Phe Arg Pro Lys Val Thr Ile Thr Ile Gln
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: CMAP27-derivative

<400> SEQUENCE: 29

Arg Lys Ile Arg Arg Phe Arg Pro Lys Val Thr Ile Thr Ile Gln
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: CMAP27-derivative

<400> SEQUENCE: 30

Lys Ile Arg Arg Phe Arg Pro Lys Val Thr Ile Thr Ile Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: CMAP27-derivative

<400> SEQUENCE: 31

Ile Arg Arg Phe Arg Pro Lys Val Thr Ile Thr Ile Gln
1               5                   10

<210> SEQ ID NO 32
<211> LENGTH: 12
<212> TYPE: PRT
<213> ORGANISM: Artificial Sequence
<220> FEATURE:
```

```
<223> OTHER INFORMATION: CMAP27-derivative

<400> SEQUENCE: 32

Arg Arg Phe Arg Pro Lys Val Thr Ile Thr Ile Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: CMAP27-derivative

<400> SEQUENCE: 33

Arg Phe Arg Pro Lys Val Thr Ile Thr Ile Gln
1               5                   10

<210> SEQ ID NO 34
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 34

Arg Trp Leu Arg Lys Ile Arg Arg Phe Arg Pro Lys Val Thr Ile Thr
1               5                   10                  15

Ile Gln

<210> SEQ ID NO 35
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 35

Arg Tyr Leu Arg Lys Ile Arg Arg Phe Arg Pro Lys Val Thr Ile Thr
1               5                   10                  15

Ile Gln

<210> SEQ ID NO 36
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 36

Arg Phe Leu Arg Lys Ile Arg Arg Trp Arg Pro Lys Val Thr Ile Thr
1               5                   10                  15

Ile Gln

<210> SEQ ID NO 37
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 37

Arg Phe Leu Arg Lys Ile Arg Arg Tyr Arg Pro Lys Val Thr Ile Thr
1               5                   10                  15

Ile Gln
```

<210> SEQ ID NO 38
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 38

```
Arg Trp Leu Arg Lys Ile Arg Arg Trp Arg Pro Lys Val Thr Ile Thr
1               5                   10                  15

Ile Gln
```

<210> SEQ ID NO 39
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 39

```
Arg Tyr Leu Arg Lys Ile Arg Arg Tyr Arg Pro Lys Val Thr Ile Thr
1               5                   10                  15

Ile Gln
```

<210> SEQ ID NO 40
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 40

```
Arg Trp Leu Arg Lys Ile Arg Arg Tyr Arg Pro Lys Val Thr Ile Thr
1               5                   10                  15

Ile Gln
```

<210> SEQ ID NO 41
<211> LENGTH: 18
<212> TYPE: PRT
<213> ORGANISM: Artificial Sequence
<220> FEATURE:
<223> OTHER INFORMATION: CMAP27-derivative

<400> SEQUENCE: 41

```
Arg Tyr Leu Arg Lys Ile Arg Arg Trp Arg Pro Lys Val Thr Ile Thr
1               5                   10                  15

Ile Gln
```

<210> SEQ ID NO 42
<211> LENGTH: 15
<212> TYPE: PRT
<213> ORGANISM: Artificial Sequence
<220> FEATURE:
<223> OTHER INFORMATION: CMAP27-derivative

<400> SEQUENCE: 42

```
Arg Lys Ile Arg Arg Trp Arg Pro Lys Val Thr Ile Thr Ile Gln
1               5                   10                  15
```

<210> SEQ ID NO 43
<211> LENGTH: 15
<212> TYPE: PRT
<213> ORGANISM: Artificial Sequence

```
<220> FEATURE:
<223> OTHER INFORMATION: CMAP27-derivative

<400> SEQUENCE: 43

Arg Lys Ile Arg Arg Tyr Arg Pro Lys Val Thr Ile Thr Ile Gln
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: CMAP27-derivative

<400> SEQUENCE: 44

Arg Arg Trp Arg Pro Lys Val Thr Ile Thr Ile Gln
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CMAP27-derivative

<400> SEQUENCE: 45

Arg Arg Tyr Arg Pro Lys Val Thr Ile Thr Ile Gln
1               5                   10
```

CATH2 DERIVATIVES

This application is a continuation of U.S. patent application Ser. No. 15/310,034, filed on Nov. 9, 2016, (now U.S. Pat. No. 10,829,524) which is a U.S. National Phase Application under 35 U.S.C. § 371 of International Application PCT/NL2015/050323, filed on May 8, 2015, which claims the benefit of EP 14167718.7, filed on May 9, 2014, the entire contents of each of which is hereby incorporated by reference in their entireties.

SEQUENCE LISTING

This application contains a Sequence Listing that has been submitted electronically as an ASCII text file named SequenceListing.txt. The ASCII text file prepared on Aug. 9, 2022, is 15,300 bytes in size. The material in the ASCII text file is hereby incorporated by reference in its entirety.

The invention relates to the field of antibiotics and immune stimulating substances, especially to peptides with such activity, more specific peptides derived from CMAP27, also known as CATH2

CATH2 or CMAP27 is a member of the genus of antimicrobial peptides. Thus far, many types of antimicrobial peptides have been isolated and sequences from various sources during past decades (for selected reviews, see: Otvos Jr., L. *Cell. Mol. Life Sci.* 2002, 59:1138; Otvos, Jr., L. J. *Peptide Sci.* 2000, 6:497; Tan, Y.-T. et al., *Mol. Med. Today* 2000, 6:309; Scott, M. G. and Hancock, R. E. W., *Crit. Rev. Immunol.* 2000, 20:407; Hancock, R. E. W. and Chapple, D. S. *Antimicrob. Agents Chemother.* 1999, 43:1317; Hetru, C. et al., In: *Molecular Mechanisms of Immune Responses in Insects*; Brey, P. and Hultmark, D. Ed., Chapman and Hall, London, 1998, pp. 40-66; Hancock, R. E. W. et al., *Adv. Microb. Physiol.* 1995 37:135; Vaara, M. *Microbiol. Rev.* 1992, 395). Within mammals and birds most antimicrobial peptides discovered up to date belong to the cathelicidin and defensin superfamily. Cathelicidins have been found to be widely distributed among divergent species, i.e. in mammals, birds, fish and reptiles, indicating their evolutionary importance, but their repertoire differs considerably among species. Antimicrobial peptides of the cathelicidin family are encoded in the genome as prepropeptides and are proteolytically cleaved to form biologically active peptides ranging from 12 to 97 amino acids (Ramanathan, B. et al., 2002, Microbes Infect. 4:361-372). Based on their typical primary and secondary structure, the released C-terminal peptides can be divided into four main classes, namely 1) α-helical peptides, linear peptides that adopt an amphipathic structure when in contact with environments mimicking biological membranes (LL-37, Agerberth, B., et al., *PNAS* 1995, 92:195; SMAP-29, Anderson, R. C., et al., *Antimicrob. Agents Chemother.* 2004, 48:673); 2) β-hairpin peptides, short cyclic peptides formed by one or two intramolecular disulfide bridges (protegrins, Kokryakov, V. N., et al., FEBS Lett. 1993, 327:231; dodecapeptide, Romeo, D., et al., *J. Biol. Chem.* 1988, 263:9573); 3) tryptophan-rich peptides (indolicidin) (Indolicidin, Selsted, M. E., et al., *J. Biol. Chem.* 1992, 267:4292) and 4) proline/arginine-rich peptides (bactenecins, Gennaro, R., et al., *Infect. Immun.* 1989, 57:3142; PR39, Agerberth, B., et al., *Eur. J. Biochem.* 1991, 202:849).

Most cathelicidins show broad activity against several Gram-negative and Gram-positive bacteria, fungi, protozoa and enveloped viruses (Zaiou, M. and Gallo, R. L., 2002, J. Mol. Med. 80:549-561). Van Dijk et al., (2005, Vet. Immunol. Immunopath. 106:321-327) found a new protein of the cathelicidin family in chicken. It belongs to the group 1 (α-helical) peptides and has been denominated CMAP27, but is also known as CATH-2. Like other members of the cathelicidin family CMAP27 is encoded as a prepropeptide (154 amino acids) and after proteolytic processing, a C-terminal peptide is released that has demonstrated potent broad spectrum antimicrobial activity. The amino acid sequence of this C-terminal peptide, called CMAP27 or CATH2, is RFGRFLRKIRRFRPKVTITIQGSARFG (SEQ ID NO: 1).

In the mean time various derivatives of CMAP27 have been synthesized and it was shown in earlier studies (see WO 2010/093245) that C-terminally truncated CMAP27 derivatives not only maintained the antibiotic properties of CMAP27 against Gram(−) bacteria, but that these also had an antibiotic effect on Gram(+) bacteria such as *S. aureus* and *B. anthracis*. Although these have been found to work well, there is still need for further active derivatives of CMAP27.

SUMMARY OF THE INVENTION

The inventors now found further derivatives of CMAP27. In one embodiment, the present invention comprises new N-terminally truncated CMAP27-derivative, while in another embodiment, the present invention comprises new inverso and retroinverso CMAP27-derivatives.

Further, the present invention comprises a method for in ovo vaccination of poultry, preferably chicken, comprising administering a CMAP27 derivative, wherein said CMAP27 derivative is selected from the group of C-terminally truncated CMAP27 derivatives, N-terminally truncated CMAP27 derivatives, D-amino acid CMAP27-derivatives, cyclic CMAP27-derivatives, inverso and retroinverso CMAP27-derivatives. Also part of the invention is a method for activating the immune response of an animal or human providing said animal or human with a CMAP27 derivative, wherein said CMAP27 derivative is selected from the group of C-terminally truncated CMAP27 derivatives, N-terminally truncated CMAP27 derivatives, D-amino acid CMAP27-derivatives, cyclic CMAP27-derivatives, inverso and retroinverso CMAP27-derivatives Preferably in said method the activation of the immune response is chosen from enhanced Toll-like receptor activation by increased DNA uptake, endotoxin neutralization, stimulation of cytokine/chemokine production by immune cells, direct chemotaxis, enhanced phagocytosis and stimulation of the proliferation and differentiation of immune cells.

Further part of the present invention is an immunologic composition comprising a CMAP27 derivative selected from the group of N-terminally truncated CMAP27-derivative, Inverso and Retroinverso CMAP27-derivatives.

Also comprised in the invention is the use of a CMAP27 derivative selected from the group of N-terminally truncated CMAP27-derivative, inverso and retroinverso CMAP27-derivatives for the preparation of a medicament for therapy of an infectious disease or for the preparation of a vaccine, specifically wherein said use is the use as an antibiotic or the increasing of weight of the animal treated with such a compound.

Further, also part of the present invention is a method for increasing the weight of poultry by in ovo vaccination of eggs of said poultry species with a CMAP27 derivative, wherein said CMAP27 derivative is selected from the group of C-terminally truncated CMAP27 derivatives, N-terminally truncated CMAP27 derivatives, D-amino acid CMAP27-derivatives, cyclic CMAP27-derivatives, inverso and retroinverso CMAP27-derivatives.

LEGEND TO THE FIGURES

FIG. 1A-1B—Differential and total counts of chicken peripheral blood leukocytes at 2 days p.i. after subcutaneous injection with $10^6$ CFU of avian pathogenic *Salmonella enteritis* pt13a. A) total counts. B) differential counts.

FIG. 2A-2B—Mortality after subcutaneous injection with $10^6$ CFU of avian pathogenic *Salmonella enteritis* pt13a. A) Survival curves of peptide treated and nontreated birds during 7 days post infection. B) Reduction of mortality (%) relative to untreated infected birds (+ control).

FIG. 3A-3B—Lesion scores determined at 7 days p.i. after subcutaneous injection with $10^6$ CFU of avian pathogenic *Salmonella enteritis* pt13a. Left and right thoracic air sacs (respiratory tract), liver and heart (systemic infection) were separately evaluated using a scoring system: 0=no lesions, 1=mild lesions, 2=moderate lesions and 3=severe lesions. The mean lesion scores (MLS) were calculated as the sum of lesion scores per bird. A) The percentage of salmonellosis positive birds (MLS>1) and the reduction of salmonellosis positive birds relative to untreated infected birds. B) The average lesion scores relative to untreated infected birds.

Figure 4A:
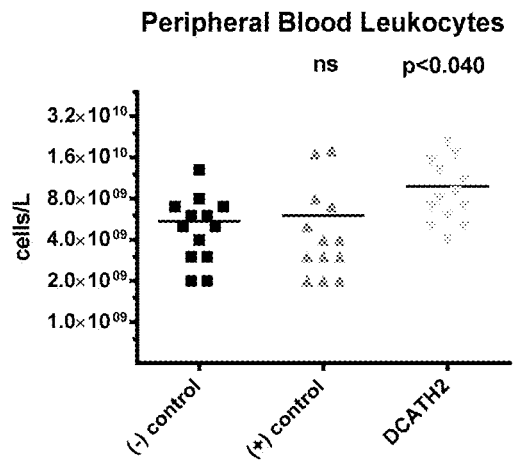
Figure 4B:
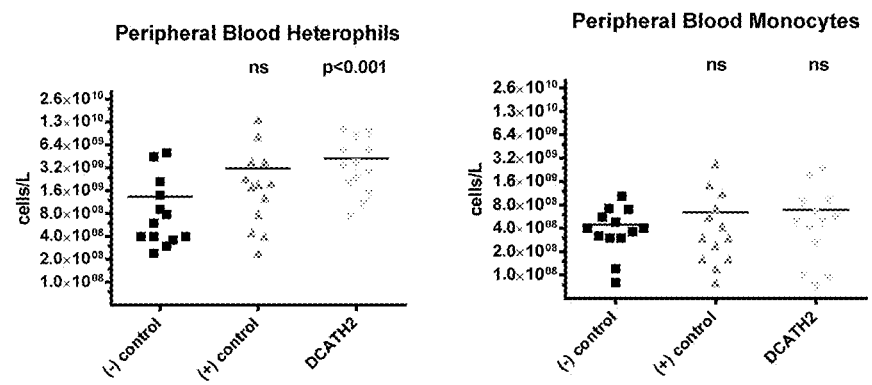

FIG. 4A-4B—Differential and total counts of chicken peripheral blood leukocytes at 2 days p.i. after intra-tracheal injection with $10^6$ CFU of avian pathogenic *E. coli* 506. A) total counts. B) differential counts.

Figure 5A:
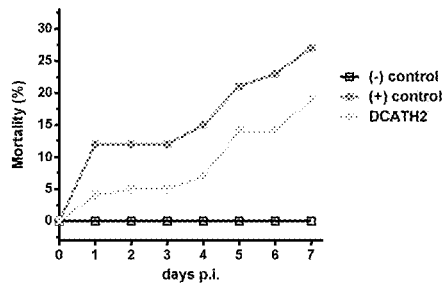
Figure 5B:
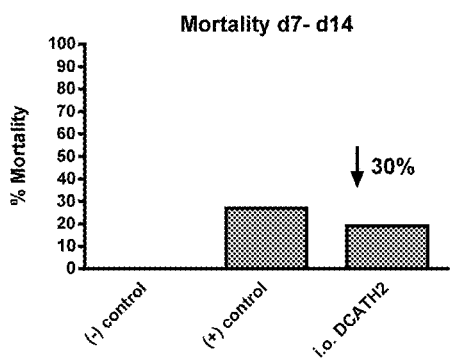

FIG. 5A-5B—Mortality after intra-tracheal injection with $10^6$ CFU of avian pathogenic *E. coli* 506. A) Survival curves of peptide treated and nontreated birds during 7 days post infection. B) Reduction of mortality (%) relative to untreated infected birds.

Figure 6A:
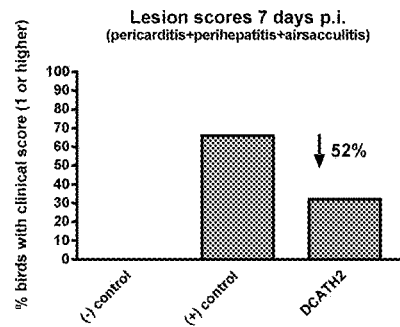
Figure 6B:
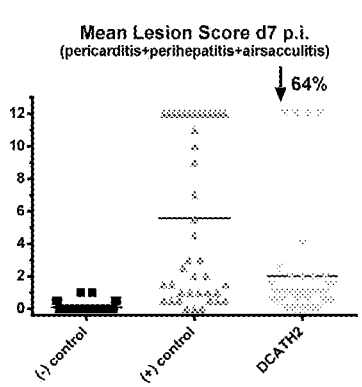

FIG. 6A-6B—Lesion scores determined at 7 days p.i. after intratracheal injection with $10^6$ CFU of avian pathogenic *E. coli* 506. Left and right thoracic air sacs (respiratory tract), liver and heart (systemic infection) were separately evaluated using a scoring system: 0=no lesions, 1=mild lesions, 2=moderate lesions and 3=severe lesions. The mean lesion scores (MLS) were calculated as the sum of lesion scores per bird. A) The percentage of colibacillosis positive birds (MLS>1) and the reduction of colibacillosis positive birds relative to untreated infected birds. B) The average lesion scores relative to untreated infected birds.

Figure 7:
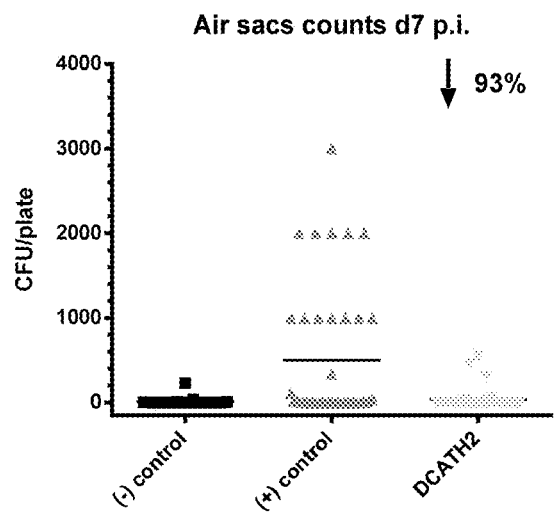

FIG. 7—Thoracic air sac counts 7 days after intratracheal injection with $10^6$ CFU of avian pathogenic *E. coli* 506.

Figure 8A:
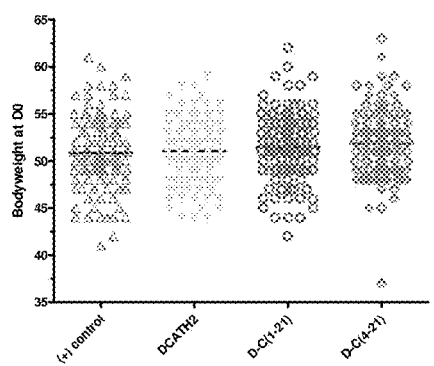
Figure 8B:
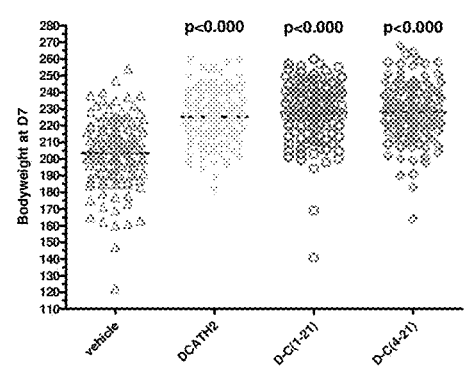

FIG. 8A-8B—Bodyweights of Ross308 broilers assessed at hatch (D0) (FIG. 8A) and at 7 days after hatch (D7) (FIG. 8B). Birds were injected at embryonic day 18 with 1 mg/kg peptide or vehicle.

Figure 9A:
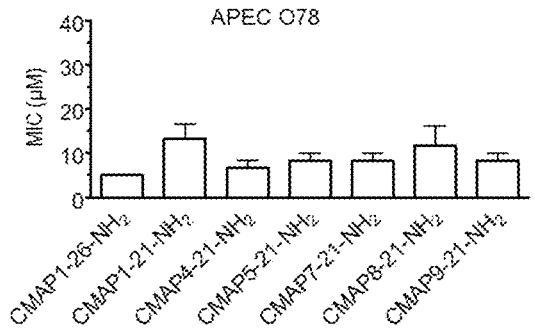
Figure 9B:
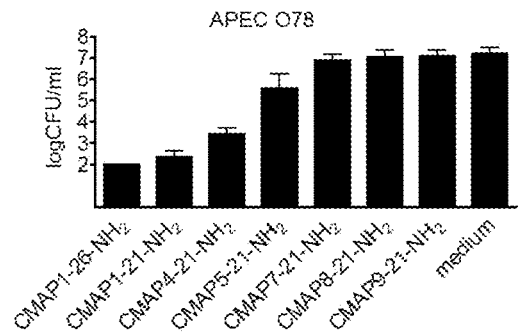
Figure 9C:
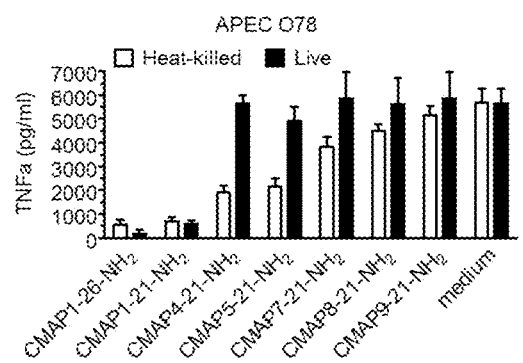

FIG. 9A-9C—Antibacterial activity of CMAP27 derived peptides in vitro against an avian pathogenic *Escherichia coli* O78 (APEC O78) field isolate. A) Antibacterial activity of peptides (5 μM) against APEC O78 ($2\times10^6$ CFU/ml) in 50% Mueller Hinton broth using colony count assays. B) Antibacterial activity of peptides (5 μM) against APEC O78 ($3\times10^5$ CFU/ml) in DMEM containing 10% fetal calf serum (FCS) using colony count assays. C) TNFα production by J774.A1 cells (ELISA) after 2 h incubation at 37° C. with live or heat-killed APEC O78 ($3\times10^5$ CFU/m) in DMEM/ 10% FCS, in the presence or absence of 5 μM peptide. Data represents means±SEM from 3 independent experiments.

Figure 10:
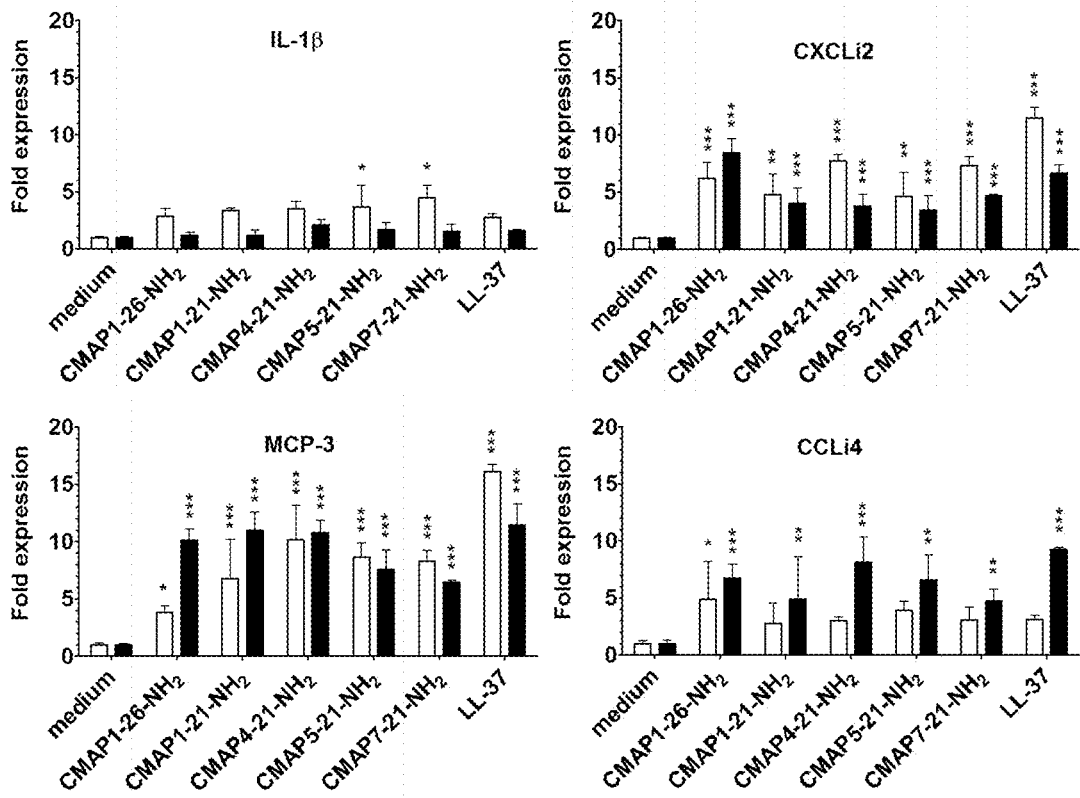

FIG. 10—Chemokine induction by CMAP27 derived peptides in HD11 cells. HD11 cells were seeded in 96 wells tissue culture treated plates ($2\times10^5$ cell/mL) in RPMI-1640/ 10% FCS and incubated at 37° C. (5% $CO_2$) with peptide (20 μM) supplemented medium during 4 h (open bars) or 24 h (closed bars). Transcription levels of interleukin-1β, IL-8 (CXCLi2), monocyte chemotactic protein-3 (MCP-3) and RANTES (CCLi4) were determined by real time PCR. Significance levels: *P<0.05, P<0.01, *P<0.001. Data represents means±SEM from 3-4 independent experiments.

FIG. 11A-11B—Neutralization of lipopolysaccharide-induced interleukin-1β induction and nitric oxide production in HD11 cells by CMAP27 derived peptides. HD11 cells were seeded in 96 wells tissue culture treated plates ($2\times10^5$ cell/mL) in RPMI-1640/10% FCS. Final concentrations of 50 ng/ml LPS were pre-incubated with or without 20 μM peptide for 30 min at 37° C. (5% $CO_2$), applied to the cells and incubated for 4 h and 24 h. A) Transcription levels of interleukin-1 were determined by real time PCR (4 h only). B) Supernatants were collected for the determination of nitric oxide production (24 h incubations only) using the Griess assay. Significance levels: *P<0.05, P<0.01, *P<0.001. Data represents means±SEM from 3-4 independent experiments.

FIG. 12A-12B—Substitution of phenylalanine residues by tryptophan enhances the in vitro LPS neutralization capacity of CMAP27 derived peptides. HD11 cells were seeded in 96 wells tissue culture treated plates ($2\times10^5$ cell/mL) in RPMI-1640/10% FCS. Final concentrations of 50 ng/ml LPS were pre-incubated with or without 20 μM peptide for 30 min at 37° C. (5% $CO_2$), applied to the cells and incubated for 4 h or 24 h. A) Transcription levels of interleukin-1 were determined by real time PCR (4 h only). B) Supernatants were collected for the determination of nitric oxide production (24 h incubations only) using the Griess assay. Significance levels: *P<0.05, P<0.01, *P<0.001. Data represents means±SEM from 3-4 independent experiments.

FIG. 13A-13B—CMAP27 derived peptides enhance DNA uptake and DNA-induced activation. A) HD11 cells were stimulated during 4 h with 2.5 nM Alexa-Fluor 488 labeled ODN-2006 in the absence and presence of CMAP27 derived peptides (5 μM), after which DNA uptake was analyzed by flow cytometry. B) Supernatants of HD11 cells stimulated for longer time (17 h) under these same conditions were collected and used for determination of nitric oxide production using the Griess assay. Data represents means±SEM from 3-4 independent experiments.

DEFINITIONS

"CMAP27" or "CATH2" as used herein is defined as the protein having the amino acid sequence RFGRFLRKIRR-FRPKVTITIQGSARFG (SEQ ID NO: 1), but also the C-terminally amidated version RFGRFLRKIRRFRPKVTI-TIQGSARF-NH$_2$ (SEQ ID NO: 2), also denominated as CMAP1-26-NH2, is comprised in this definition. It is suggested that CMAP1-26-NH2 is the active form of the peptide, since it is known in cathelicidins that amidation of the C-terminal glycine residue adds to the functionality (Shinnar, A. E. et al., 2003, Bioorg. Chem. 31:425-436; Tomasinsig, I. And Zanetti, M, 2005, Curr. Prot. Pept. Sci. 6:23-34).

The term "peptide" as used herein means a sequence of amino acids coupled by a peptide bond, wherein the amino acids are one of the twenty naturally peptide-building amino acids and wherein one or all of the amino acids can be in the L-configuration or in the D-configuration, or, for isoleucine and threonine in the D-allo configuration (only inversion at one of the chiral centers). A peptide according to the invention can be linear, i.e. wherein the first and last amino acids of the sequence have a free NH$_2$- or COOH-group respectively or are N-terminally (acetylation) and/or C-terminally (amidation) modified.

"C-terminally truncated CMAP27-derivatives" are herein defined as those truncated peptides that have been described in WO 2010/093245, especially the peptides listed as CMAP26-NH2, CMAP26, CMAP26 (P14→G), CMAP26 (P14→L), CMAP1-21, CMAP1-15, CMAP1-15 (F2→L), CMAP1-15 (F5→L), CMAP1-15 (F12→L), CMAP1-15 (3xF→L), CMAP1-15 (F2→W), CMAP1-15 (F5→W), CMAP1-15 (F12→W), CMAP1-15 (F2→W: F5→W: F12→W), CMAP1-13, CMAP1-12, CMAP1-11 and CMAP1-10 in Table 1 of said document and their acetylated and/or amidated derivatives. Further preferred are CMAP1-21 (F2→W), CMAP1-21 (F5→W), CMAP1-21 (F12→W), CMAP1-21 (F2, 5→W), CMAP1-21 (F5, 12→W), CMAP1-21 (F2, 12→W), CMAP1-21 (F2, 5, 12→W), CMAP1-21 (F2→Y), CMAP1-21 (F5→Y), CMAP1-21 (F12→Y), CMAP1-21 (F2, 5→Y), CMAP1-21 (F5, 12→Y), CMAP1-21 (F2, 12→Y), CMAP1-21 (F2, 5, 12→Y), CMAP1-21 (F2→W; F5→Y), CMAP1-21 (F2∝Y: F5→W), CMAP1-21 (F5→W: F12→Y), CMAP1-21 (F5→Y: F12→W), CMAP1-21 (F2→W: F12→Y), CMAP1-21 (F2→Y: F12→W), CMAP1-21 (F2→W: F5→Y: F12→Y), CMAP1-21 (F2→Y: F5→W: F12→Y), and CMAP1-21 (F2→Y: F12→Y: F12→W). The CMAP proteins identified above, may also be indicates as CATH2 peptides. CMAP1-21 then would be CATH2(1-21).

"N-terminally truncated CMAP27 derivatives" are CMAP-27 derivatives that are truncated at the N-terminal amino acid (arginine) of CMAP27. Especially mentioned are the derivatives selected from the group consisting of N-terminally truncated variants of CMAP1-21: CMAP4-21, CMAP5-21, CMAP6-21, CMAP7-21, CMAP8-21, CMAP9-21, CMAP10-21, CMAP11-21, CMAP4-21 (F5→W), CMAP4-21 (F5→Y), CMAP4-21 (F12→W), CMAP4-21 (F12→Y), CMAP4-21 (F5, F12→W), CMAP4-21 (F5, F12→Y), CMAP4-21 (F5→W, F12→Y), CMAP4-21 (F5→Y, F12→W), CMAP7-21 (F12→W), CMAP7-21 (F12→Y), CMAP10-21 (F12→W) and CMAP10-21 (F12→Y).

"D-amino acid CMAP27-derivatives" or "D-amino acid CATH2-derivatives" are CMAP-27/CATH2 derivatives as defined herein (including the above defined C- and N-terminally truncated CMAP27-derivatives) that contain at least one amino acid in the D configuration. A special category of these D-amino acid CMAP27/CATH2 derivatives are the peptides that are composed of only D amino acids (i.e. in which no L amino acid is present). This special category is herein defined as D-only CMAP27-derivatives. Also CMAP27/CATH2 itself, comprising one or more, or, alternatively, all D amino acids is comprised within this definition.
Preferred D-amino acid CMAP27-derivatives are the following full D-amino acid CATH2-derivatives (where all amino acids are in the D-form):

|  |  |
|---|---|
| D-C(1-26) (DCATH2) | RFGRFLREIRRFRPKVTITIQGSARF-NH$_2$ (SEQ ID NO: 3) |
| D-C(1-21) | RFGRFLREIRRFRPKVTITIQ-NH$_2$ (SEQ ID NO: 4) |
| D-C(4-21) | RFLREIRRFRPKVTITIQ-NH$_2$ (SEQ ID NO: 5) |
| D-C(7-21) | REIRRFRPKVTITIQ-NH$_2$ (SEQ ID NO: 6) |
| D-C(7-21)F/W | REIRRWRPKVTITIQ-NH$_2$ (SEQ ID NO: 7) |
| D-C(7-21)F/Y | REIRRYRPKVTITIQ-NH$_2$ (SEQ ID NO: 8) |
| D-C(10-21)F/W | RRWRPKVTITIQ-NH$_2$ (SEQ ID NO: 9) |
| D-C(1-15) | RFGRFLRKIRRFRPK-OH (SEQ ID NO: 10) |

"Cyclic CMAP27-derivatives" or "cyclic CAH2-derivatives" are CMAP27/CATH2 derivatives in which at least two of the non-adjacent amino acids are connected to form a ring structure. Although in principle any chemical binding construction may be used, such as replacing two non-adjacent amino acids in any of the above-mentioned CMAP27 derivatives with a cysteine, where these cysteines then form an S—S bridge, a preferred binding system uses the binding between Bpg (Fmoc-L-bishomopropargylglycine) and an azido-resin, wherein the Bpg is attached to an internal arginine, leucine, phenylalanine or tryptophane residue and the azido-resin is attached to the C-terminal glutamic acid residue. Especially, such cyclic derivatives are:

|  |  |
|---|---|
| cycCMAP(1-21)[Lys8] | RFGRFLR(Bpg)IRRFRPKVTITIQ (azido-resin) (SEQ ID NO: 11) |
| cycCMAP(1-21)[Arg7] | RFGRFL(Bpg)KIRRFRPKVTITIQ (azido-resin) (SEQ ID NO: 12) |
| cycCMAP(1-21)[Leu6] | RFGRF(Bpg)RKIRRFRPKVTITIQ (azido-resin) (SEQ ID NO: 13) |
| cycCMAP(1-21)[Leu6], Phe2/Trp | RWGRF(Bpg)RKIRRFRPKVTITIQ (azido-resin) (SEQ ID NO: 14) |
| cycCMAP(1-21)[Leu6], Phe2,5/Trp | RWGRW(Bpg)RKIRRFRPKVTITIQ (azido-resin) (SEQ ID NO: 15) |
| cycCMAP(1-21)[Leu6], Phe2,5,12/Trp | RWGRW(Bpg)RKIRRWRPKVTITIQ (azido-resin) (SEQ ID NO: 16) |
| cycCMAP(1-21)[Leu6], Phe5,12/Trp | RFGRW(Bpg)RKIRRWRPKVTITIQ (azido-resin) (SEQ ID NO: 17) |
| cycCMAP(1-21)[Leu6], Phe12/Trp | RFGRF(Bpg)RKIRRWRPKVTITIQ (azido-resin) (SEQ ID NO: 18) |

"Inverso" and "retroinverso" or, respectively" 'I'-CMAP27 and "RI"-CMAP27-derivatives ("I"-CATH2 and "RI"-CATH2 derivatives) are peptides that have an inverted sequence with respect to the above-mentioned CMAP27-derivatives, in the sense that the amino acids are connected to each other in a reverse order. The I and RI equivalent of CMAP27/CATH2 then become GFRASGQITITVKPRFR-RIKRLFRGFR (SEQ ID NO: 19) and other preferred examples of such I or RI-CMAP27-derivatives are:

| | |
|---|---|
| RI-C(1-21) | (SEQ ID NO: 20) QITITVKPRFRRIKRLFRGFR |
| RI-C(4-21) | (SEQ ID NO: 21) QITITVKPRFRRIKRLFR |
| RI-C(7-21) | (SEQ ID NO: 22) QITITVKPRFRRIKR |
| RI-C(7-21)F/W | (SEQ ID NO: 23) QITITVKPRWRRIKR |
| RI-C(7-21)F/Y | (SEQ ID NO: 24) QITITVKPRYRRIKR |
| RI-C(10-21)F/W | (SEQ ID NO: 25) QITITVKPRWRR |

Of course the I and RI-CMAP27 derivatives may be acetylated at their N-terminal and/or amidated at their C-terminal. When the inverted CMAP27 derivatives contain one or more D amino acids they are termed "retroinverso" or "RI". If the inverted derivative only contains L-amino acids it is termed "inverso" or "I".

The peptides of the invention can be produced synthetically or, where applicable, recombinantly by conventional methods. Specific embodiments of CMAP27-derived antibiotic peptides are disclosed in detail in the experimental part below. Preferably, the peptides or peptide derivatives of the invention are prepared conventionally by known chemical synthesis techniques, such as, for instance, are disclosed by Merrifield (J. Am. Chem. Soc. (1963) 85:2149-2154). They may be isolated from the reaction mixture by chromatographic methods, such as reverse-phase HPLC.

Alternatively, the peptides of the invention may be produced by recombinant DNA techniques by cloning and expressing within a host micro-organism or cell a DNA fragment carrying a nucleic acid sequence encoding one of the above-described peptides. Nucleic acid coding sequences can be prepared synthetically, or may be derived from existing nucleic acid sequences (e.g. the sequence coding for wild-type CATH2) by site-directed mutagenesis. These nucleic acid sequences may then be cloned in a suitable expression vector and transformed or transfected into a suitable host cell, such as *E. coli, Bacillus, Lactobacillus, Streptomyces*, mammalian cells (such as CHO, HEK or COS-1 cells), yeasts (e.g. *Saccharomyces, Schizophyllum*), insect cells or viral expression systems, such as baculovirus systems, or plant cells. A person skilled in the art will have knowledge of the techniques of constructing the nucleic acid sequences and providing means to enable their expression.

Specifically plant cells could be used advantageously for expression of the peptides of the invention, since the peptide in such a case could orally be administered to a human or animal directly, i.e. without any further purification.

Subsequently, the peptide can be isolated from the culture of the host cells. This can be achieved by common protein purification and isolation techniques, which are available in the art. Such techniques may e.g. involve immunoadsorption or chromatography. It is also possible to provide the peptides with a tag (such as a histidine tag) during synthesis, which allows for a rapid binding and purification, after which the tag is enzymatically removed to obtain the active peptide.

Alternatively, the peptides can be produced in cell-free systems, such as the Expressway™ cell-free system of Invitrogen.

Some more comprehensive summaries of methods which can be applied in the preparation of the peptides are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Novel peptides as disclosed herein can be readily made by a person skilled in the art.

The CMAP27- or CATH2-derivatives of the invention may be used alone, or in combination in the form of multimers. Suitable combinations of peptides of the invention comprise concatemers of peptides of the invention serially coupled to each other via spacers, for instance in the form of a peptide dimer, a peptide trimer, etc., wherein the individual peptides are subsequently aligned. Single peptide or peptidomimetic chains may be coupled to a biocompatible protein, such as human serum albumin, humanized antibody, liposome, micelle, synthetic polymer, nanoparticle, and phage. Alternatively, multimers of individually combined peptides of the invention may be prepared in the form of dendrimers, or clusters, wherein three or more peptides are linked to one common center.

Yet other combinations in the form of multimers may be formed by beads on the surface of which the peptides of the invention are exposed. The bead may then function as a carrier for the peptide, and may similarly function as a detectable label. Multimers can, for example, be prepared by biotinylating the N-terminus of peptide chains and subsequent complexation with streptavidin. As streptavidin is able to bind 4 biotin molecules or conjugates with high affinity, very stable tetrameric peptide complexes can be formed by this method. Multimers may be composed of identical or different peptides or peptidomimetics according to the invention. Preferably, however, the multimers of the invention are composed of two or more peptides or peptidomimetics, in which each component constitutes to one asset of the total biocidal activity (targeting, antimicrobial activity, scavenging).

A pharmaceutical composition of the invention comprises a therapeutically effective amount of one or more CMAP27 derivatives of the present invention. Once formulated, the pharmaceutical compositions of the invention can be administered directly to the subject in a method of treating bacterial infection comprising administering to a subject in need thereof a therapeutically effective amount of the composition of the invention. Also, the pharmaceutical compositions of the invention may be used in a method of modulating the immune system.

Direct delivery of the compositions will generally be accomplished by topical application or other forms of administration, either orally, parenterally, subcutaneously, sublingually, intralesionally, intraperitoneally, intravenously or intramuscularly, pulmonarily, or delivered to the interstitial space of a tissue.

One especially envisaged method of administration is providing the CMAP-27 derivative in ovo. With "in ovo administration" is meant administration to eggs of an avian species, preferably eggs in the fourth quarter of incubation. That is, for chicken eggs, the administration is conducted preferably on about the fifteenth to nineteenth day of incubation, and more preferably on about the eighteenth day of incubation. For turkey eggs, the administration is conducted preferably on about the twenty-first to twenty-sixth day of incubation, and more preferably on about the twenty-fifth day of incubation. Such an administration can be conducted by any method which results in the introduction of one or more of the CMAP-27 derivatives into an egg through the shell. A preferred method of administration is by injection. The injection can be performed by using any one of the well-known egg injection devices, such as a conventional hypodermic syringe fitted with a needle of about 18 to 22 gauge, or a high speed automated egg injection system as described in U.S. Pat. Nos. 4,681,063, 4,040,388, 4,469,047, and 4,593,646.

The pharmaceutical composition may also comprise a suitable pharmaceutically acceptable carrier or diluent and may be in the form of a capsule, tablet, lozenge, dragee, pill, droplet, suppository, powder, spray, vaccine, ointment, paste, cream, inhalant, patch, aerosol, and the like. As pharmaceutically acceptable carrier, any solvent, diluent or other liquid vehicle, dispersion or suspension aid, surface active agent, isotonic agent, thickening or emulsifying agent, preservative, encapsulating agent, solid binder or lubricant can be used which is most suited for a particular dosage form and which is compatible with the peptide or peptide conjugate.

A pharmaceutical composition may thus contain a pharmaceutically acceptable carrier. The term "pharmaceutically acceptable carrier" also includes a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Salts of peptides or functional equivalents are prepared by known methods, which typically involve the mixing of the peptide with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for ex vivo applications can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates are encompassed.

Pharmaceutically acceptable salts can be used herein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

The derivatives of the invention may be administered alone or in combination with pharmaceutically acceptable carriers or diluents by the routes previously indicated and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of (phospho)lipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyphenyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels. For therapeutic treatment, the peptide or peptide-conjugate may be produced as described above and applied to the subject in need thereof. The peptide or peptide-conjugate may be administered to a subject by any suitable route, preferably in the form of a pharmaceutical composition adapted to such a route and in a dosage that is effective for the intended treatment.

Pharmaceutical compositions of this invention may contain other active agents, such as conventional antibiotics (like e.g. vancomycin, streptomycin, tetracyclin, penicillin) or other antimicrobial compounds, such as anti-fungals, e.g. itraconazole or myconazole. Also compounds that alleviate other infection symptoms, such as fever (e.g. salicylic acid) or skin rash may be added.

Therapeutically effective dosages of the peptide or peptide-conjugate required for treating a bacterial infection in the body of a human or animal subject, can easily be determined by the skilled person, for instance by using animal models.

The term "therapeutically effective amount" as used herein refers to an amount of a therapeutic, viz. a peptide or peptide-conjugate according to the present invention, to reduce or prevent growth and colonization of bacteria, or to exhibit a detectable therapeutic or prophylactic effect. The effect can be detected by, for example, culturing biopsies and assaying for bacterial activity or by any other suitable method of assessing the progress or severity of bacterial infection. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician or experimenter. Specifically, the compositions of the present invention can be used to reduce or prevent bacterial infection and/or accompanying biological or physical manifestations, such as reduction of fever. Methods that permit the clinician to establish initial dosages are known in the art. The dosages determined to be administered must be safe and efficacious.

For purposes of the present invention, an effective dose will be from about 0.01 µg/kg to 50 mg/kg, preferably 0.5 µg/kg to about 10 mg/kg of the peptide or peptide-conjugate in the individual to which it is administered. Dosages for achieving the therapeutic effects of the pharmaceutical composition described herein may easily be determined by the skilled person. For in ovo applications the same doses may be used, but recalculated with relation to the weight of the embryo.

Yet in another alternative embodiment, the peptide or peptide-conjugate or compositions of the invention may be administered from a controlled or sustained release matrix inserted in the body of the subject.

It may also be advantageous to administer a compound of the invention in a transmucosal dosage form. This route of administration is non-invasive and thus less cumbersome for the subject that is being treated and for the person that is providing the treatment; at the same time it may lead to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, cholesterol and its derivatives, ethanol, fatty acids, oleic acid, fatty acid derivatives, EDTA, carbomers, polycarbophil, and chitosan.

Indications for which the CMAP27-derivatives of the invention can be used are bacterial infections by both Gram-positive and Gram-negative bacteria, such as *E. coli, Agrobacterium tumefaciens, Salmonella typhimurum, Erwinia carotovora, E. herbicola, E. chrysanthemi, Klebsiella pneumoniae, Haemophilus influenzae, Francisella tularensis, Archanobacterium pyogenes, Avibacterium paragallinarum, Bacillus anthracis, Bacillus megaterium, Bacillus anthracis, Bordetelle* spp., *Brachyspira* spp., *Brucella* spp., *Campylobacter* spp., *Clostridium botulinum, Clostridium perfringens, Clostridium septicum, Corynebacterium pyogenes, Coxiella burnetii, Enterococcus* spp., *Haemophilus somnus, Yersinia pestis, Listeria monocytogenes, Mannheimia haemolytica, Mycobacterium tuberculosis, Mycobacterium avium, Mycoplasma gallisepticum, Mycoplasma synoviae, Ornithobacterium rhinotracheale, Pasteurella aeruginosa, Pastuerella multocida, Pneumococcus* spp. *Pseudomonas aeruginosa, Riemerella anatipestifer, Salmonella* spp., *Streptococcus uberis, Streptococcus* spp., *Staphylococcus aureus, Staphylococcus pyrogenes, Truperella pygoenes, Vibria cholerae, Micrococcus luteus, Moraxella, Neisseria gonorrhoeae, Aerobacter, Borellia.* Apart from bacterial infections, also other infections, like infections with viruses, fungi, yeasts and parasites may be treated with the peptides of the invention.

The effectiveness of the compounds of the present invention is not only provided by their antibiotic effect, but also by their immunomodulatory effects. Further, the newly discovered immunoactivating effects (see below) provide a further advantage of the present compounds.

Next to therapeutic use for treatment of infections, it is also possible to use the antibiotic peptides of the invention in a bactericidal composition that can be used to clean surfaces and/or equipment. Another field of application is in packaging, where peptides can be linked to or embedded in packaging material for packaging of food or other material that is easily degradable by micro-organisms. The CMAP27 derivatives of the invention are specifically usable for packaging, since they are not toxic upon contact or ingestion.

Especially useful is the application of the CMAP27 derivatives in veterinary applications, especially in poultry. Salmonella enteritidis infection can lead to substantial mortality and morbidity in young chickens. In particular, the first two weeks after hatching, when their acquired immune system is not yet sufficiently developed broiler chicks are highly susceptible. A possible strategy to improve the health status of broiler chickens is to boost their innate immune system in order to bridge the gap between fading maternal protection and maturation of adaptive immunity. The immune modulating properties of chicken cathelicidin-2 (CATH2 or CMAP27) derivatives in vitro have indicated that the compounds of the invention may be used to boost the innate immune response of young chicken broilers. This may be achieved by in ovo vaccination of chicken embryos or by vaccination of young chickens. Surprisingly, such in ovo vaccination also has the effect that is known from antibiotic treatment during growth and development of poultry, preferably (broiler) chicken, i.e. an increase in the body weight as compared to non-treated animals. Hence, this one-time in ovo vaccination can replace the use of antibiotics during the growth of the animals.

In these and other veterinary applications, the composition comprising the CATH2 or CMAP27 derivative further comprises a veterinary acceptable carrier. Such a veterinary-acceptable carrier may include solvents, dispersion media, coatings, adjuvants, stabilizing agents, diluents, preservatives, antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others.

Adjuvants suitable for use in the present method include but are not limited to: mineral gels, e.g., aluminum hydroxide; surface active substances such as lysolecithin; glycosides, e.g., saponin derivatives such as Quil A or GPI-0100 (U.S. Pat. No. 5,977,081); cationic surfactants such as DDA, pluronic polyols; polyanions; non-ionic block polymers, e.g., Pluronic F-127 (B.A.S.F., USA); peptides; mineral oils, e.g. Montanide ISA-50 (Seppic, Paris, France), carbopol, Amphigen (Hydronics, Omaha, Nebr. USA), Alhydrogel (Superfos Biosector, Frederikssund, Denmark) oil emulsions, e.g. an emulsion of mineral oil such as BayoF/Arlacel A and water, or an emulsion of vegetable oil, water and an emulsifier such as lecithin; alum, cholesterol, rmLT, cytokines and combinations thereof. The immunogenic component may also be incorporated into liposomes, or conjugated to polysaccharides and/or other polymers for use in a vaccine formulation. Additional substances that can be included in a product for use in the present methods include, but are not limited to one or more preservatives such as disodium or tetrasodium salt of ethylenediaminetetracetic acid (EDTA), merthiolate, and the like. Immunostimulants which enhance the immune system's response to antigens may also be included in a product. Examples of suitable immunostimulants include cytokines such as IL-12 or IL-2, or stimulatory molecules such as muramyl dipeptide, aminoquinolones, lipopolysaccharide, and the like.

It has been found that the N-terminally truncated CMAP-27 derivatives as defined above still maintain an antibacterial effect, but that they also maintain their immunomodulatory effect. This immunomodulatory effect shows by the ability of the N-terminally truncated CMAP-27 derivatives to neutralize LPS-induced proinflammatory cytokine (IL-1ß) transcription. It has, however, further been found that all of the CMAP-27 derivatives, including the N-terminally truncated derivatives as described above show immunoactivating activity, which distinguishes them from already known (N-terminally truncated) CMAP27 derivatives. These immunoactivating effects may comprise many mechanisms including enhanced Toll-like receptor activation by increased DNA uptake, stimulation of cytokine/chemokine production by immune cells, direct chemotaxis, enhanced phagocytosis and stimulation of the proliferation and differentiation of immune cells and are distinct from the previously disclosed immunomodulatory and antibiotic effects of the peptide derivatives.

It is part of the present invention that these immunoactivating effects, especially the effect on the proliferation and differentiation of immune cells is a strong advantage for the compounds when used in vaccination, especially for in ovo vaccination.

EXAMPLES

Example 1—Efficacy of CMAP-27 Derivative Peptides Administered in Ovo

DCATH2 peptide (the full D-amino acid analog of CMAP1-26) was suspended in a cholesterol/PBS formulation. Ross308 eggs were injected in the amnion fluid at 18 days of embryonic age with 100 µl of DCATH2 containing suspension and returned to an egg incubator to hatch (~ at 21 days embryonic age). Both control groups were injected in the amnion fluid with cholesterol/PBS formulation. The 1 mg/kg bodyweight dose of peptide was calculated based on an embryo body weight of 22 g. After hatch, birds were transferred into 4 pens per treatment (n=40/group). Three days after hatch, all birds except the negative control were subcutaneously inoculated with an avian pathogenic Salmonella enteritidis pt13a strain at a dose of $5 \times 10^6$ CFU per bird. Two day after challenge, 12 birds per group were sacrificed and used to take samples for blood and organ analysis. Blood samples were taken to determine total leukocyte counts and leukocyte differentiation. During the 7 day challenge period mortality was registered per day. At the end of the challenge period at 7 days post infection, all remaining birds were sacrificed and in the left and right side thoracic air sacs, liver and heart were examined for lesion scores.

Analysis of blood smears obtained at 2 days post injection revealed that the total number of peripheral blood leukocytes was significantly elevated in broiler chicks treated with the compounds of the invention compared to non-infected birds (FIG. 1A). This increase was absent in untreated infected birds. Manual counting of leukocytes in Giemsa stained blood smears revealed that the absolute number of peripheral blood heterophils was significantly higher in DCATH2 treated birds compared to non-infected birds (FIG. 1B). Heterophil numbers were not affected by infection status.

Heterophils are the avian counterpart of the mammalian neutrophil and it has been shown that in chickens heterophils play a pivotal role in protection against bacterial infections.

The development of Salmonellosis and severity of *Salmonella*-related lesions were determined during a 7 day period. Upon *Salmonella enteritidis* challenge mortality increased gradually up to 35% for untreated infected birds. A delay up to 3 days p.i. was observed for DCATH2 treated birds (FIG. 2A). At 7 days p.i. mortality was reduced by 50% for DCATH2 treated birds (FIG. 2B).

The percentage of salmonellosis positive birds, i.e. having a mean lesion score>1, in the untreated infected group was approximately 85%; this was reduced by 53% in the DCATH2 treated group A (FIG. 3A). In addition, the severity of lesions in salmonellosis positive birds was decreased by 69% in DCATH2-treated birds (FIG. 3B).

In conclusion, in ovo treatment with 1 mg/kg of DCATH2 peptide decreased *Salmonella*-induced mortality at 7 days p.i. by 50%, reduced among surviving birds the number of salmonellosis positive birds by 53% and reduced the severity of lesions by 69%. The decreased susceptibility for *Salmonella* challenge in DCATH2 treated birds may in part be explained by increased heterophil recruitment and hematopoiesis.

Example 2—Protection Against *E. coli* Infection after in Ovo Administration of Peptide DCATH2 peptide was suspended in a Cholesterol/PBS formulation. Ross308 eggs were injected in the amnion fluid at 18 days of embryonic age with 100 µl of DCATH2 containing suspension and returned to an egg incubator to hatch (~ at 21 days embryonic age). Both control groups were injected in the amnion fluid with cholesterol/PBS formulation. The 1 mg/kg bodyweight dose of DCATH2 peptide was calculated based on an embryo body weight of 22 g. After hatch, birds were transferred into isolator units per treatment (n=54/group). Three days after hatch, all birds except the negative control were intratracheally inoculated with an avian pathogenic *Escherichia coli* 506 strain (UU strain) at a dose of $1 \times 10^6$ CFU per bird. Two day after challenge, 13 birds per group were sacrificed and used to take samples for blood and organ analysis. Blood samples were taken to determine total leukocyte counts and leukocyte differentiation. During the 7 day challenge period mortality was registered per day. At the end of the challenge period at 7 days post infection, all remaining birds were sacrificed and in the left and right side thoracic air sacs, liver and heart were examined for lesion scores.

Figure 4B:
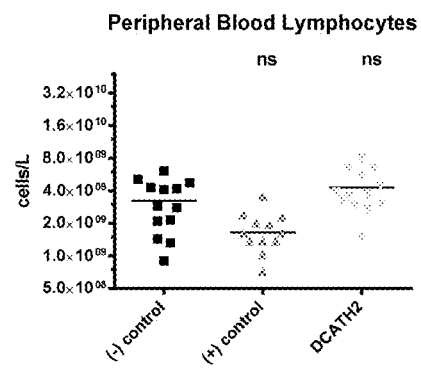

The development of colibacillosis was determined over a 7 day period. At 2 days p.i., DCATH2 in ovo treated birds showed significantly higher absolute numbers of peripheral blood leukocytes and heterophils compared to untreated non-infected birds (FIG. 4). No differences were found for the absolute numbers of monocyte and lymphocyte numbers in DCATH2 treated birds if compared to non-treated, non-infected animals.

*E. coli* challenge resulted in a gradual increasing mortality up to 27% for the untreated infected birds (FIG. 5A). At 7 days p.i. mortality was reduced by 30% for DCATH2 in ovo treated birds (FIG. 5B).

The percentage of colibacillosis positive birds was 65% in the untreated infected group; this was reduced by 52% in DCATH2 treated birds (FIG. 6A). The severity of colibacillosis-related lesions was reduced by 64% in CATH2 treated birds (FIG. 6B). Moreover, air sac colonization by *E. coli* was also reduced by 93% by in ovo treatment; with DCATH2 (FIG. 7).

In conclusion, in ovo treatment with 1 mg/kg of DCATH2 peptide decreased (respiratory tract) *E. coli*-induced mortality at 7 days p.i. by 30%, reduced among surviving birds the number of colibacillosis positive birds by 52%, reduced the severity of lesions by 64% and reduced air sac colonization by *E. coli* by 93%. The decreased susceptibility for *E. coli* challenge in DCATH2 treated birds may in part be explained by increased heterophil recruitment and hematopoiesis.

Example 3—Weight Gain by in Ovo Treatment of Chicken

DCATH2 peptide and truncated analogs D-CMAP(1-21) and D-CMAP(4-21) were suspended in a Cholesterol/PBS formulation. Ross308 eggs were injected in the amnion fluid at 18 days of embryonic age with 100 µl of peptide containing suspension and returned to an egg incubator to hatch (~ at 21 days embryonic age). Both control groups were injected in the amnion fluid with cholesterol/PBS formulation. The 1 mg/kg bodyweight dose of peptide was calculated based on an embryo body weight of 22 g. After hatch, all birds were weighed individually (D0) and transferred into isolator units per treatment (n=120/group). Birds were fed ad libitum and at 7 days after hatch (D7) bodyweights of individual birds were assessed.

Peptide treatment at 18 days of embryonic age did not affect hatchability (Table 1).

In ovo peptide treatment at 18 days of embryonic development did not significantly affect the bodyweight of broiler chicks at hatch (D0, FIG. 8A). However, at 7 days post hatch birds that had been treated in ovo with 1 mg/kg of peptide DCATH2, D-CMAP(1-21) or D-CMAP(4-21) showed significant higher body weights compared to vehicle treated birds (FIG. 8B).

TABLE 1

Efficacy experiment III. Hatchability of Ross308 eggs injected with 1 mg/kg peptide or vehicle at day 18 embryonic of embryonic development.

| IN OVO TREATMENT | HATCHABILITY |
| --- | --- |
| vehicle | 98% |
| 1 mg/kg DCATH2 | 97% |
| 1 mg/kg D-C(1-21) | 95% |
| 1 mg/kg D-C(4-21) | 94% |

Example 4—Antibacterial Activity of CMAP27 Derived Peptides In Vitro

The avian pathogenic *Escherichia coli* O78 (APEC O78) field isolate used to demonstrate in ovo efficacy of DCATH2 peptide was used to examine antibacterial activity of CMAP27 derived peptides in vitro. Cultures grown overnight in Mueller-Hinton broth (MHB) at 37° C. were diluted to a concentration of $2 \times 10^6$ CFU/ml in 50% Mueller-Hinton broth and mixed in 96 wells polypropylene microwell plates at a 1:1 ratio with peptide (final concentration of 1.25 to 40 µM). After 3 h incubation samples were serially diluted in medium, spread on trypton soy agar media and counted after 24 h incubation. All peptides tested exhibited antibacterial activity against the APEC O78 field isolate with minimal inhibitory concentrations ranging from 5 to 14 µM (FIG. 9A).

To test if peptides would be able to inhibit bacteria under more challenging conditions, e.g. in the presence of salts and serum proteins, APEC O78 was incubated with peptide in DMEM medium containing 10% fetal calf serum. In brief, bacterial survival was estimated by incubating $3\times10^5$ CFU/ml APEC O78 during 2 h at 37° C. in DMEM/10% FCS in the presence or absence of 5 µM peptide, after which serial dilutions were made, spread on agar media and colonies were enumerated after 24 h incubation at 37° C. In contrast to testing in MHB medium, among the peptides tested in DMEM containing 10% fetal calf serum only CMAP1-26-$NH_2$, CMAP1-21-$NH_2$ and CMAP4-21-$NH_2$ substantially inhibited bacterial growth (FIG. 9B), in the case of CMAP1-26-$NH_2$ to below the detection limit of 100 cells/ml.

Peptide-mediated inhibition of macrophage activation induced by live or heat-killed APEC O78, was examined using J774.A1 cells, a murine macrophage cell line. For this purpose, J774.A1 cells (150,000 cells/well) cultured in DMEM containing 10% FCS were exposed during 2 h at 37° C. to $3\times10^5$ CFU/ml APEC O78 with or without 5 µM peptide, after which supernatants were collected and used to determine TNFα production (ELISA). Under these conditions, both live and heat-killed (30' at 70° C.) bacteria strongly induced TNFα production by J774.A1 cells in the absence of peptide (FIG. 9C). Peptides CMAP1-26-$NH_2$ and CMAP1-21-$NH_2$ substantially inhibited TNFα production induced by live and heat-killed bacteria.

Further N-terminal truncation of CMAP1-21-$NH_2$ resulted in a gradual loss of inhibition of the TNFα production induced by heat-killed bacteria and in a complete loss of inhibition of the TNFα production induced by live bacteria. TNFα production induced by heat-killed bacteria was also inhibited to some extent by peptides lacking antibacterial activity under these conditions, e.g. CMAP7-21-$NH_2$.

In conclusion, CMAP27 derived peptides exhibit antibacterial activity in vitro, including conditions with relative high salt and serum proteins. Direct antibacterial activity is rapidly lost upon further N-terminal truncation of peptide CMAP1-21-$NH_2$. Furthermore, this loss of antibacterial activity correlates with the capacity of peptides to inhibit the TNFα production produced by live bacteria.

Example 5—Chemokine Induction in HD11 Cells

HD11 cells, a chicken macrophage cell line, were seeded in 96 wells tissue culture treated plates ($2\times10^5$ cell/mL) in RPMI-1640/10% FCS and incubated at 37° C. (5% $CO_2$) with peptide (20 µM) supplemented medium during 4 h or 24 h. Transcription levels of interleukin-1β, -8 (CXCLi2), monocyte chemotactic protein-3 (MCP-3) and RANTES (CCLi4) were determined by real time PCR.

CMAP1-26-$NH_2$ was found to induce transcription of chemokines CXCLi2/IL-8, MCP-3 and CCLi4/RANTES in HD11 cells, whereas proinflammatory cytokine IL-1β was not induced (FIG. 10). Truncated analogs were examined for their capacity to induce chemokine transcription in HD11 cells. N-terminal truncated analogs of CMAP1-21-$NH_2$ up to 15 amino acid residues, i.e. CMAP7-21-$NH_2$, maintained a capacity to induce CXCLi2 and MCP-3 transcription. Prolonged stimulation (24 h) was needed to induce expression of CCLi4.

In conclusion, the selective induction of chemokine expression in HD11 cells by CMAP-derived peptides indicates that these peptides have indirect chemotactic effects on monocytes/macrophages and suggests that in vivo these peptides may participate in this way in the recruitment and activation of immune cells.

As a positive control LL-37, a human cathelicidin peptide (see e.g. Durr, U. H. et al., 2006, Biochim. Biophys. Acta 1758:1408-1425; Zuijderduijn, S. et al., 2006, J. Allergy Clin. Immunol. 117:1328-1335) has been used.

Example 6—Anti-Inflammatory Activity of CMAP27 Derived Peptides In Vitro

HD11 cells were seeded in 96 wells tissue culture treated plates ($2\times10^5$ cell/mL) in RPMI-1640/10% FCS. Final concentrations of 50 ng/ml Salmonella minnesota LPS were pre-incubated with or without 20 µM peptide for 30 min at 37° C. (5% $CO_2$), applied to the cells and incubated for 4 h and 24 h. A) Transcription levels of interleukin-1 were determined by real time PCR (4 h only). B) Supernatants were collected for the determination of nitric oxide production (24 h incubations only) using the Griess assay.

LPS-induced IL-1β expression in HD11 cells was blocked by CMAP1-26-$NH_2$ peptide (90.8%) and truncated analogs CMAP1-21-$NH_2$ (93.5%) and CMAP4-21-$NH_2$ (80.5%) (FIG. 11A). Peptides CMAP1-26-$NH_2$ and CMAP1-21-$NH_2$ blocked resp. 96.2% and 78.9% of LPS-induced (50 ng/ml) NO production while CMAP4-21-$NH_2$ neutralized NO production by 51% (FIG. 11B).

Substitution of phenylalanine by tryptophan residues in truncated analogs significantly enhanced their capacity to block LPS-induced IL-1β expression in HD11 cells (FIG. 12A), improving peptide CMAP4-21-$NH_2$ mediated inhibition from 80.5% to 95.1%. Moreover, whereas peptides CMAP7-21-$NH_2$ and CMAP10-21-$NH_2$ lack LPS-neutralizing activity, their Phe/Trp substituted analogs strongly inhibited LPS-induced proinflammatory cytokine production by HD11 cells, i.e. 86.3% and 71.9%, respectively. In addition, substitution of phenylalanine by tryptophan in truncated CMAP27 derived peptides appeared to increase the capacity of C(1-21) and C(4-21) to inhibit LPS-induced NO production (FIG. 12B).

In conclusion, CMAP27 derived peptides are capable of neutralizing lipopolysaccharide-induced production of proinflammatory mediators such as IL-1β and nitric oxide and in that way may dampen an excessive inflammatory response. Moreover, substitution of phenylalanine residues can be used to enhance/introduce the anti-inflammatory capacity of CMAP27 derived peptides.

Example 7—CMAP27 Derived Peptides Enhance Uptake of and Activation of Immune Cells by DNA To study effects of peptides on the uptake of DNA, HD11 cells were seeded $3\times10^5$ cells in 24-wells plates, stimulated during 4 h with 2.5 nM Alexa-Fluor 488 labeled ODN-2006 in the absence and presence of CMAP27 derived peptides (5 µM), after which DNA uptake was analyzed by flow cytometry. Activation of HD11 cells was examined by collecting supernatants after 17 h under the same conditions and determination of nitric oxide production.

CMAP27 derived peptides CMAP1-26-$NH_2$, CMAP1-21-$NH_2$, CMAP4-21-$NH_2$, CMAP-21-$NH_2$, and CMAP7-21-$NH_2$ all enhanced the uptake of ODN-2006 by HD11 cells (FIG. 13A) as well as increasing the DNA-induced nitric oxide production (FIG. 13B). Augmented DNA uptake and DNA-induced activation were correlated, indicating that the enhanced uptake of DNA by CMAP27 derived peptides is a crucial step in enhancing the DNA-induced activation.

In conclusion, in the presence of CMAP27 derived peptides bacterial CpG-DNA may be more readily detected by immune cells at infections.

The invention claimed is:

1. An N-terminally truncated CMAP27-derivative, wherein said derivative is selected from the group consisting of CMAP4-21 (SEQ ID NO: 26), CMAP5-21 (SEQ ID NO: 27), CMAP6-21 (SEQ ID NO: 28), CMAP7-21 (SEQ ID NO: 29), CMAP8-21 (SEQ ID NO: 30), CMAP9-21 (SEQ ID NO: 31), CMAP10-21 (SEQ ID NO: 32), CMAP11-21 (SEQ ID NO: 33), CMAP4-21 (F5→W) (SEQ ID NO: 34), CMAP4-21 (F5→Y) (SEQ ID NO: 35), CMAP4-21 (F12→W) (SEQ ID NO: 36), CMAP4-21 (F12→Y) (SEQ IS NO: 37), CMAP4-21 (F5, F12→W) (SEQ ID NO: 38), CMAP4-21 (F5, F12→Y) (SEQ ID NO: 39), CMAP4-21 (F5→W, F12→Y) (SEQ ID NO: 40), CMAP4-21 (F5→Y, F12→W) (SEQ ID NO: 41), CMAP7-21 (F12→W) (SEQ ID NO: 42), CMAP7-21 (F12→Y) (SEQ ID NO: 43), CMAP10-21 (F12→W) (SEQ ID NO: 44) and CMAP10-21 (F12→Y) (SEQ ID NO: 45), wherein CMAP27 has the amino acid sequence of SEQ ID NO: 1.

2. A method for in ovo vaccination of poultry, comprising administering a CMAP27 derivative according to claim 1.

3. The method according to claim 2, wherein the poultry is chicken.

4. A method of activating the immune response of an animal of a human, the method comprising administering a CMAP27-derivative according to claim 1 to said animal or human.

5. The method according to claim 4, wherein the activation of the immune response is chosen from enhanced Toll-like receptor activation by increased DNA uptake, endotoxin neutralization, stimulation of cytokine/chemokine production by immune cells, direct chemotaxis, enhanced phagocytosis and stimulation of the proliferation and differentiation of immune cells.

6. A pharmaceutical composition comprising a CMAP27 derivative as claimed in claim 1 and a pharmaceutically acceptable carrier.

7. A method of preventing an infectious disease in a subject comprising administering to said subject a vaccine comprising a CMAP27 derivative as claimed claim 1.

8. A method for treating bacterial infection in a subject comprising administering a CMAP27 derivative according to claim 1 to said subject.

9. A method for increasing weight in an animal comprising administering a CMAP27 derivative according to claim 1 to said animal.

10. A method for increasing the weight of poultry by in ovo vaccination of eggs of said poultry species with a CMAP27 derivative according to claim 1.

* * * * *

UNITED STATES PATENT AND TRADEMARK OFFICE
CERTIFICATE OF CORRECTION

| | |
|---|---|
| PATENT NO. | : 11,603,391 B2 |
| APPLICATION NO. | : 17/069127 |
| DATED | : March 14, 2023 |
| INVENTOR(S) | : Hendrik Peter Haagsman, Albert van Dijk and Edwin Johannes Adrianus Veldhuizen |

It is certified that error appears in the above-identified patent and that said Letters Patent is hereby corrected as shown below:

On the Title Page

Column 2 (Other Publications), Line 16, delete "Veterinaiy" and insert -- Veterinary --

In the Claims

Column 39, Line 41, Claim 1, delete "IS" and insert -- ID --

Column 40, Line 44, Claim 7, after "claimed" insert -- in --

Signed and Sealed this
Ninth Day of April, 2024

*Katherine Kelly Vidal*

Katherine Kelly Vidal
*Director of the United States Patent and Trademark Office*